(12) United States Patent
Tajiri et al.

(10) Patent No.: US 11,872,017 B2
(45) Date of Patent: Jan. 16, 2024

(54) DETECTING DEVICE AND MEASURING DEVICE

(71) Applicant: SEIKO EPSON CORPORATION, Tokyo (JP)

(72) Inventors: Takashi Tajiri, Matsumoto (JP); Takefumi Fukagawa, Nagano-Ken (JP)

(73) Assignee: SEIKO EPSON CORPORATION, Tokyo (JP)

(*) Notice: Subject to any disclaimer, the term of this patent is extended or adjusted under 35 U.S.C. 154(b) by 0 days.

(21) Appl. No.: 18/173,742

(22) Filed: Feb. 23, 2023

(65) Prior Publication Data

US 2023/0270338 A1    Aug. 31, 2023

(30) Foreign Application Priority Data

Feb. 28, 2022  (JP) .................. 2022-029121

(51) Int. Cl.
*A61B 5/024* (2006.01)
*G06V 40/13* (2022.01)
*A61B 5/00* (2006.01)

(52) U.S. Cl.
CPC ........ *A61B 5/0077* (2013.01); *A61B 5/02438* (2013.01); *G06V 40/1318* (2022.01)

(58) Field of Classification Search
CPC .............. G06V 40/1318; A61B 5/0077; A61B 5/02438; A61B 5/00; A61B 5/0059; A61B 5/02427; A61B 5/14532; A61B 5/1455; A61B 5/14552; A61B 5/681
See application file for complete search history.

(56) References Cited

U.S. PATENT DOCUMENTS

| | | | |
|---|---|---|---|
| 6,333,544 B1 * | 12/2001 | Toyoda | H01L 27/1443 257/E27.128 |
| 2016/0240721 A1 * | 8/2016 | Chu | G01J 1/0214 |
| 2017/0337412 A1 * | 11/2017 | Bhat | G06V 40/1318 |
| 2018/0360341 A1 * | 12/2018 | Wang | A61B 5/0008 |
| 2020/0327302 A1 * | 10/2020 | He | G06F 3/0421 |

FOREIGN PATENT DOCUMENTS

WO    2018066519    4/2018

* cited by examiner

*Primary Examiner* — Antonio Xavier
(74) *Attorney, Agent, or Firm* — JCIPRNET

(57) ABSTRACT

A detecting device includes a flexible substrate, a first light-emitting unit provided at the flexible substrate and configured to emit light toward a living body, and a first light-receiving unit provided at the flexible substrate and configured to receive light, based on the light exiting from the first light-emitting unit, from the living body. The first light-emitting unit is constituted by a flexible organic light-emitting diode, and the first light-receiving unit is constituted by a flexible organic photodetector.

7 Claims, 10 Drawing Sheets

DETECTING DEVICE AND MEASURING DEVICE

The present application is based on, and claims priority from JP Application Serial Number 2022-029121, filed Feb. 28, 2022, the disclosure of which is hereby incorporated by reference herein in its entirety.

BACKGROUND

1. Technical Field

The present disclosure relates to a detecting device and a measuring device.

2. Related Art

Various measurement technologies for non-invasively measuring biological information such as heartbeats have been known in the related art.

For example, WO 2018/066519 describes an electrode sheet including a flexible substrate that is sheet-like, and a biological signal acquisition unit disposed on the flexible substrate and configured to acquire a biological signal of a living body. The biological signal acquisition unit includes a light-emitting unit configured to irradiate the living body with light of a predetermined wavelength, and a light-receiving unit configured to receive reflected light of the light emitted by the light-emitting unit. The light-emitting unit and the light-receiving unit are covered by a protective layer that curves along a curvature of the living body.

However, the light-emitting unit and the light-receiving unit described in WO 2018/066519 are covered by the protective layer curved along the curvature of the living body, increasing a distance between the light-emitting unit and the human body and a distance between the light-receiving unit and the human body. As these distances increase, an amount of light reflected by the human body decreases and an amount of light received by the light-receiving unit decreases.

SUMMARY

A detecting device according to an aspect of the present disclosure includes a flexible substrate, a first light-emitting unit provided at the flexible substrate and configured to emit light toward a living body, and a first light-receiving unit provided at the flexible substrate and configured to receive light, based on the light exiting from the first light-emitting unit, from the living body. The first light-emitting unit is constituted by a flexible organic light-emitting diode, and the first light-receiving unit is constituted by a flexible organic photodetector.

A measuring device according to an aspect of the present disclosure includes the detecting device according to the one aspect, and an information analysis unit configured to identify biological information from a detection signal indicating a detection result obtained by the detecting device.

DESCRIPTION OF EXEMPLARY EMBODIMENTS

Preferred exemplary embodiments of the present disclosure will be described in detail hereinafter with reference to the accompanying drawings. Note that the exemplary embodiments described hereinafter are not intended to unjustly limit the content of the present disclosure as set forth in the claims. In addition, all of the configurations described below are not necessarily essential constituent requirements of the present disclosure.

1. Measuring Device

1.1. Overall Configuration

Figure 1:
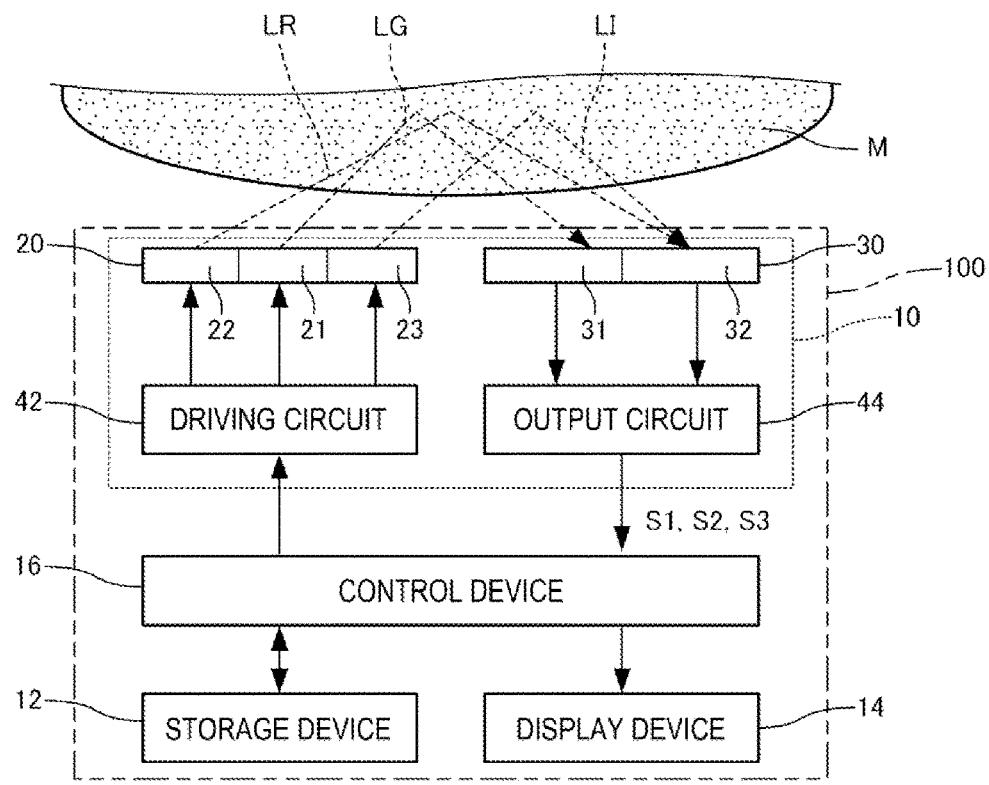
FIG. 1 is a functional block diagram of a measuring device according to an exemplary embodiment.

First, a measuring device according to this exemplary embodiment will be described below with reference to the accompanying drawings. FIG. 1 is a functional block diagram of a measuring device 100 according to the exemplary embodiment.

The measuring device 100 is a biological measuring device that non-invasively measures biological information of a living body M as a measurement target. Examples of the living body M include a human body. The living body M is a subject whose biological information is measured. Examples of a measurement site of the living body M include a fingertip and a wrist.

The measuring device 100 measures, for example, a heartbeat and an oxygen saturation (SpO2) of the living body M as biological information. The heartbeat is a pulse rate, and indicates a change in an internal volume of a blood vessel over time due to pulsation of the heart. The oxygen saturation indicates the proportion (%) of hemoglobin bound to oxygen in hemoglobin in the blood of the living body M and is an index for evaluating the respiratory function of the living body M.

As illustrated in FIG. 1, the measuring device 100 includes, for example, a detecting device 10, a storage device 12, a display device 14, and a control device 16. The detecting device 10, the storage device 12, the display device 14, and the control device 16 are accommodated in a housing (not illustrated), for example.

The detecting device 10 is an optical sensor module that generates detection signals S1, S2, S3 according to the state of the living body M. The detecting device 10 includes, for example, a light-emitting unit 20, a light-receiving unit 30, a driving circuit 42, and an output circuit 44.

The light-emitting unit 20 emits light, causing the light to exit from the light-emitting unit 20. The light exiting from the light-emitting unit 20 is incident on the living body M, propagates in the living body M while being repeatedly reflected and scattered, and then exits to the detecting device 10 side, reaching the light-receiving unit 30. In this way, the light-receiving unit 30 receives light from the living body M based on the light exiting from the light-emitting unit 20.

The light-emitting unit 20 includes, for example, a first portion 21, a second portion 22, and a third portion 23. The first portion 21, the second portion 22, and the third portion 23 emit light having different wavelengths to the living body M.

The first portion 21 of the light-emitting unit 20 emits green light LG having, for example, a green wavelength band from 520 nm to 550 nm toward the living body M. A peak wavelength of the green light LG is, for example, 520 nm.

The second portion 22 of the light-emitting unit 20 emits red light LR having, for example, a red wavelength band from 600 nm to 800 nm toward the living body M. A peak wavelength of the red light LR is, for example, 660 nm.

The third portion 23 of the light-emitting unit 20 emits near-infrared light LI having, for example, a near-infrared wavelength band from 800 nm to 1300 nm toward the living body M. A peak wavelength of the near-infrared light LI is, for example, 905 nm.

The light-receiving unit 30 includes, for example, a fourth portion 31 and a fifth portion 32.

The fourth portion 31 of the light-receiving unit 30 receives the green light LG that has propagated in the living body M after exiting from the first portion 21 of the light-emitting unit 20 and generates a signal according to an intensity of the received light.

The fifth portion 32 of the light-receiving unit 30 receives at least one of the red light LR that has propagated in the living body M after exiting from the second portion 22 of the light-emitting unit 20 and the near infrared light LI that has propagated in the living body M after exiting from the third portion 23 of the light-emitting unit 20, and generates a signal corresponding to an intensity of the received light.

The driving circuit 42 supplies a driving current, causing the light-emitting unit 20 to emit light. For example, the driving circuit 42 causes the first portion 21, the second portion 22, and the third portion 23 of the light-emitting unit 20 to periodically emit light by time-division. The driving circuit 42 is constituted by, for example, an integrated circuit (IC).

The output circuit 44 is configured to include, for example, an analog-to-digital converter (A/D converter) that converts a signal generated by the light-receiving unit 30 from analog to digital, and an amplifier circuit that amplifies the detection signal after conversion. The output circuit 44 generates detection signals S1, S2, S3 with respect to different wavelengths. The output circuit 44 is constituted by, for example, an IC.

Note that one or both of the driving circuit 42 and the output circuit 44 can also be installed as circuits external to the detecting device 10. That is, the detecting device 10 need not include the driving circuit 42 and the output circuit 44.

The detection signal S1 generated by the output circuit 44 is a signal indicating the received light intensity when the fourth portion 31 of the light-receiving unit 30 receives the green light LG. The detection signal S2 is a signal indicating the received light intensity when the fifth portion 32 of the light-receiving unit 30 receives the red light LR. The detection signal S3 is a signal indicating the received light intensity when the fifth portion 32 receives the near-infrared light LI. The amounts of light absorption by blood during dilation and contraction of blood vessels generally differ. Therefore, each detection signal S1, S2, S3 is a heartbeat signal including periodic fluctuations corresponding to pulsations, that is, volume heartbeats, of the artery in the living body M.

The storage device 12 is constituted by, for example, random access memory (RAN) or read only memory (ROM). The storage device 12 stores a program executed by the control device 16 and various data used by the control device 16.

The display device 14 is constituted by, for example, a liquid crystal display (LCD), an organic electroluminescence (EL) display, or an electrophoretic display (EPD). The display device 14 displays the biological information specified from the detection signals S1, S2, S3.

The control device 16 is an arithmetic processing device such as a central processing unit (CPU) or a field-programmable gate array (FPGA), for example. Note that the functions of the control device 16 may be configured to be distributed to a plurality of integrated circuits, or may be configured by a dedicated electronic circuit. Further, the control device 16 including the storage device 12 can also be realized by, for example, an application specific integrated circuit (ASIC).

The control device 16 identifies biological information of the living body M from the detection signals S1, S2, S3 generated by the detecting device 10 by executing the program stored in the storage device 12. Specifically, the control device 16 identifies a pulse-to-pulse interval (PPI) of the subject from the detection signal S1 indicating the intensity of the green light LG. Furthermore, the control device 16 identifies the oxygen saturation of the living body M by analyzing the detection signal S2 indicating the intensity of the red light LR and the detection signal S3 indicating the intensity of the near-infrared light LI.

As described above, in the measuring device 100, the control device 16 functions as an information analysis unit that identifies biological information from the detection signals S1, S2, S3 indicating the detection results of the detecting device 10. The control device 16 displays the biological information identified from the detection signals S1, S2, S3 on the display device 14.

Not that the control device 16 can also notify the user of the measurement result by voice output. The control device 16 may notify the user of a warning of a possibility of impaired physical function when the pulse rate or oxygen saturation has fluctuated to values out of a predetermined range.

Such a measuring device 100 as described above is applied to, for example, a smart watch or an activity meter.

1.2. Detecting Device

Figure 2:
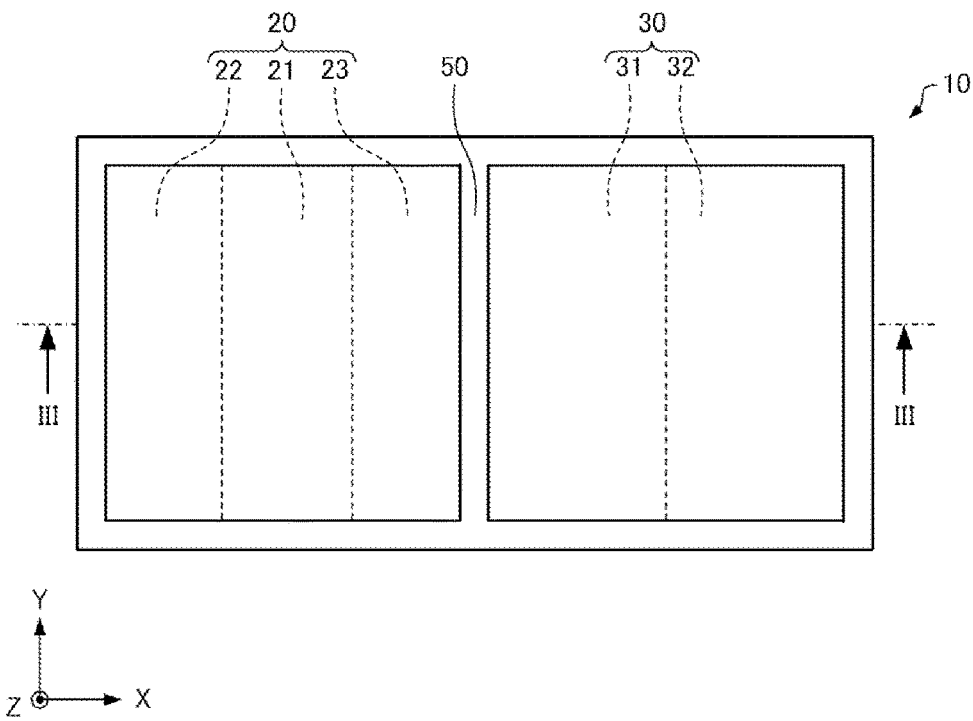
FIG. 2 is a plan view schematically illustrating a detecting device according to the exemplary embodiment.
Figure 3:
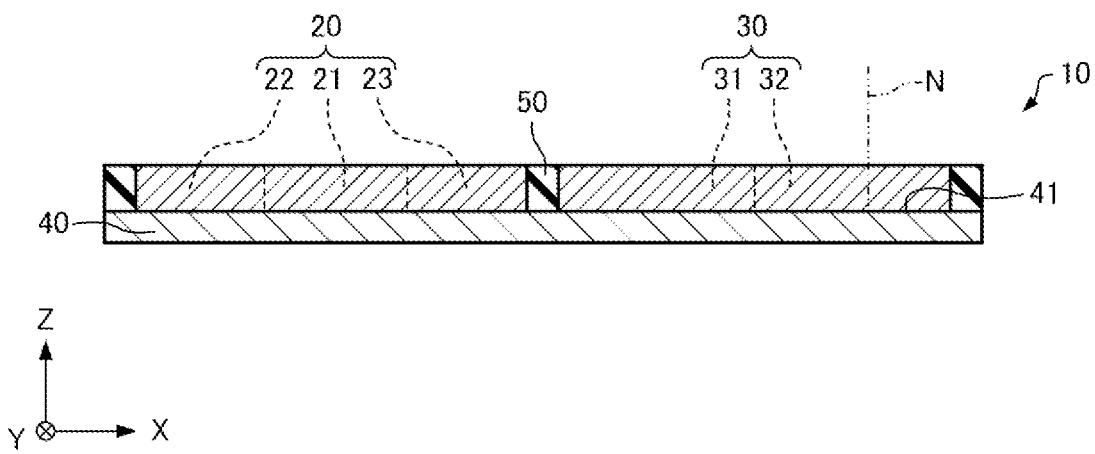
FIG. 3 is a cross-sectional view schematically illustrating the detecting device according to the exemplary embodiment.
Figure 4:
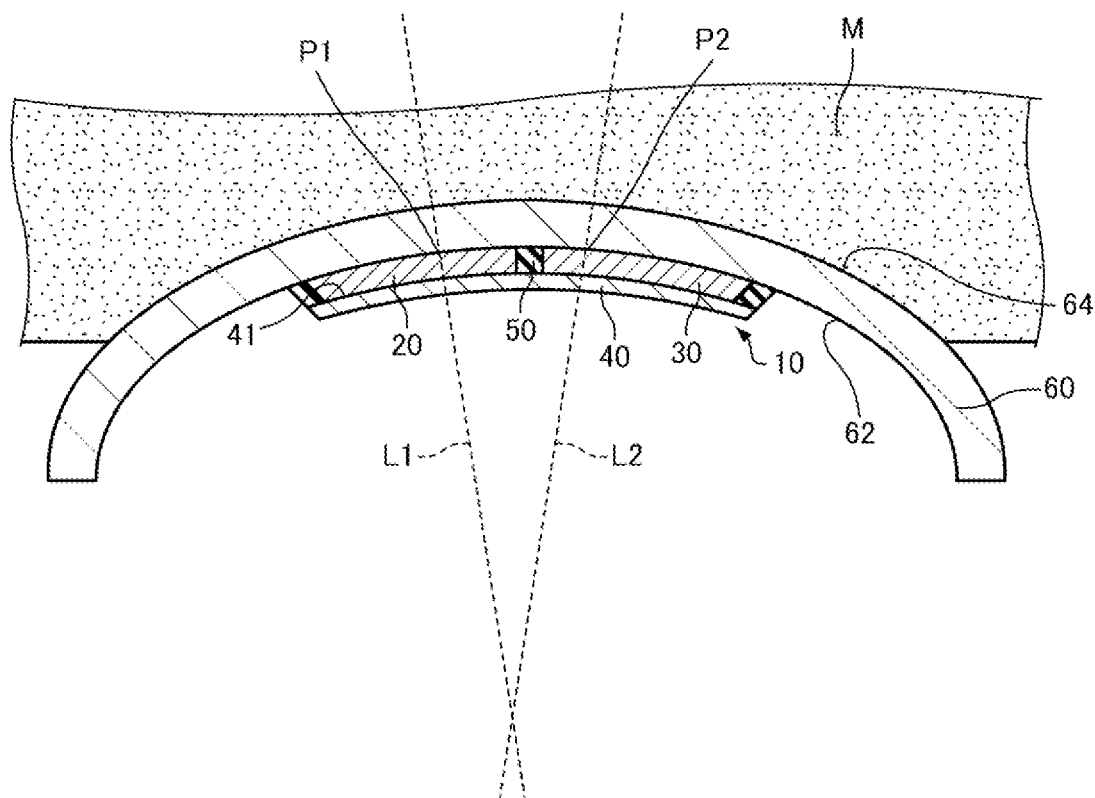
FIG. 4 is a cross-sectional view schematically illustrating a usage state of the detecting device according to the exemplary embodiment.

FIG. 2 is a plan view schematically illustrating the detecting device 10. FIG. 3 is a cross-sectional view taken along line III-III of FIG. 2, schematically illustrating the detecting device 10. FIG. 4 is a cross-sectional view schematically illustrating a usage state of the detecting device 10. Note that, in FIG. 2 and FIG. 3, an X-axis, a Y-axis, and a Z-axis are illustrated as three axes perpendicular to each other.

As illustrated in FIG. 4, when measuring biological information of the living body M, the detecting device 10 is used by being adhered to, for example, a cover member 60. When adhered to the cover member 60, the detecting device 10 can be deformed in accordance with a shape of the cover member 60.

Note that, in FIG. 1, illustration of the cover member 60 is omitted for the sake of convenience. Further, the detecting device 10 may be used by being deformed and directly adhered to the living body M without using the cover member 60.

As illustrated in FIG. 2 to FIG. 4, the detecting device 10 includes, for example, the light-emitting unit 20, the light-receiving unit 30, a flexible substrate 40, and a spacer member 50.

As illustrated in FIG. 4, when the detecting device 10 is adhered to the cover member 60, the flexible substrate 40 can be deformed in accordance with a shape of the cover member 60. For example, the flexible substrate 40 may be a flexible printed circuit (FPC). The flexible substrate 40 includes, for example, the flexible driving circuit 42 and the output circuit 44.

The shape of the flexible substrate 40 is, for example, a quadrangle such as a rectangle or a square when viewed from a normal N direction of the flexible substrate 40. Here, the "normal N direction of the flexible substrate 40" refers to a direction of a line perpendicular to a main surface 41 of the flexible substrate 40 when the flexible substrate 40 is placed on a flat surface and pulled by a predetermined force that prevents the flexible substrate 40 from becoming slack. In the example illustrated in FIG. 2 and FIG. 3, the normal N direction is the Z-axis direction. FIG. 2 and FIG. 3 illustrate the detecting device 10 in a state of not being adhered to the cover member 60.

The light-emitting unit 20 is provided on the flexible substrate 40. The light-emitting unit 20 is provided on the main surface 41 of the flexible substrate 40. As illustrated in FIG. 4, the main surface 41 is a surface of the flexible substrate 40 on the cover member 60 side when the detecting device 10 is adhered to the cover member 60. In the example illustrated in FIG. 2, a shape of the light-emitting unit 20 is a quadrangle such as a rectangle or a square when viewed from the Z-axis direction. The light-emitting unit 20 and the light-receiving unit 30 are aligned in the X-axis direction. The light-emitting unit 20 emits light toward the living body M. The light-emitting unit 20 and the light-receiving unit 30 can be deformed in the X-axis direction into a curved shape bent into an arc protruding in the Z-axis direction. The X-axis direction is a first direction. When adhered to the living body M, the light-emitting unit 20 and the light-receiving unit 30 are deformed into a curved shape bent into an arc in the first direction.

The light-emitting unit 20 is constituted by a flexible organic light-emitting diode (OLED). The light-emitting unit 20 is capable of surface emission. As illustrated in FIG. 4, when the detecting device 10 is adhered to the cover member 60, the light-emitting unit 20 can be deformed in accordance with the shape of the cover member 60. In the illustrated example, the light-emitting unit 20 is adhered to the cover member 60. The light-emitting unit 20 is formed on the flexible substrate 40 by, for example, a semiconductor thin film formation process.

The light-emitting unit 20 includes, for example, the first portion 21 that emits the green light LG, the second portion 22 that emits the red light LR, and the third portion 23 that emits the near-infrared light LI. In the example illustrated in FIG. 2 and FIG. 3, the first portion 21, the second portion 22, and the third portion 23 are aligned in the X-axis direction, and the first portion 21 is provided between the second portion 22 and the third portion 23. The third portion 23 is provided between the first portion 21 and the light-receiving unit 30 in the X-axis direction. Further, the spacer 50 is provided between the third portion 23 and the light-receiving unit 30 in the X-axis direction.

The first portion 21, the second portion 22, and the third portion 23 of the light-emitting unit 20 include an organic light-emitting layer. Depending on the type of dopant in the organic light-emitting layer, the first portion 21, the second portion 22, and the third portion 23 can emit light of different wavelengths.

Note that the first portion 21, the second portion 22, and the third portion 23 of the light-emitting unit 20 may be caused to emit light of different wavelengths by including a common organic light-emitting layer that emits white light and color filters that transmit light of different wavelengths. In this case, the color filter is made of a flexible material.

The light-receiving unit 30 is provided on the main surface 41 of the flexible substrate 40. In the example illustrated in FIG. 2, a shape of the light-receiving unit 30 is a quadrangle such as a rectangle or a square when viewed from the Z-axis direction. The light-receiving unit 30 can receive light from the living body M based on the light exiting from the light-emitting unit 20.

The light-receiving unit 30 is constituted by a flexible organic photodetector. Examples of the organic photodetector constituting the light-receiving unit 30 include a flexible organic photodiode (OPD) and a flexible organic phototransistor. As illustrated in FIG. 4, when the detecting device 10 is adhered to the cover member 60, the light-emitting unit 30 can be deformed in accordance with the shape of the cover member 60. In the illustrated example, the light-emitting unit 30 is adhered to the cover member 60. The light-emitting unit 30 is formed on the flexible substrate 40 by, for example, a semiconductor thin film formation process.

The light-receiving unit 30 includes, for example, the fourth portion 31 that receives the green light LG from the living body M and the fifth portion 32 that receives at least one of the red light LR and the near infrared light LI from the living body M. The fifth portion 32 can receive, for example, both the red light LR and the near-infrared light LI. In the example illustrated in FIG. 2 and FIG. 3, the fourth portion 31 and the fifth portion 32 are aligned in the X-axis direction. In the X-axis direction, the fourth portion 31 is provided between the light-emitting unit 20 and the fifth portion 32. Further, the spacer 50 is provided between the fourth portion 31 and the light-emitting unit 20 in the X-axis direction.

Note that the arrangement of the first portion 21, the second portion 22, and the third portion 23 of the light-emitting unit 20, and the fourth portion 31 and the fifth portion 32 of the light-receiving unit 30 is not particularly limited as long as the fourth portion 31 can receive the green light LG from the living body M exiting from the first portion 21, and the fifth portion 32 can receive the red light LR from the living body M based on the light exiting from the second portion 22 and the near-infrared light LI based on the light exiting from the third portion 23.

The spacer member 50 is provided on the flexible substrate 40. The spacer member 50 is provided on the main surface 41 of the flexible substrate 40. The spacer member 50 is provided between the light-emitting unit 20 and the light-receiving unit 30. As illustrated in FIG. 2, the spacer member 50 is further provided around the light-emitting unit 20 and around the light-receiving unit 30 when viewed from the planar Z-axis direction.

The spacer member 50 is made of a flexible material. The spacer member 50 may be formed integrally with the flexible substrate 40. As illustrated in FIG. 4, when the detecting device 10 is adhered to the cover member 60, the spacer member 50 can be deformed in accordance with the shape of the cover member 60. In the illustrated example, the spacer member 50 is adhered to the cover member 60. The spacer member 50 is formed on the flexible substrate 40 by, for example, a semiconductor process.

As illustrated in FIG. 4, the cover member 60 comes into contact with the living body M when the biological information of the living body M is measured. The cover member 60 has light transmissivity. The light exiting from the light-emitting unit 20 is transmitted through the cover member 60 and is incident on the living body M. The light from the living body M passes through the cover member 60 and is received by the light-receiving unit 30. A material of the cover member 60 is, for example, acrylic resin or polycarbonate. The detecting device 10 need not include the cover member 60, or may include the cover member 60.

The cover member 60 includes a first surface 62 and a second surface 64. The detecting device 10 is adhered to the first surface 62. The detecting device 10 may be adhered to the first surface 62 via an adhesive (not illustrated) having light transmissivity. The second surface 64 comes into contact with the living body M. The second surface 64 is a surface on a side opposite to the first surface 62.

The cover member 60 has a convex shape in which the first surface 62 faces inward and the second surface 64 faces outward. For example, in a cross-sectional view such as illustrated in FIG. 4, a virtual straight line L1 orthogonal to a tangent line at a point P1 on the second surface 64 and a virtual straight line L2 orthogonal to a tangent line at a point P2 on the second surface 64 intersect with each other on the second surface 64 side. The virtual straight line L1 and the virtual straight line L2 do not intersect on the first surface 62 side. The point P1 is a point of contact with the light-emitting unit 20 on the second surface 64. The point P2 is a point of contact with the light-receiving unit 30 on the second surface 64. The light-emitting unit 20, the light-receiving unit 30, the flexible substrate 40, and the spacer member 50 can be deformed in accordance with the shape of the cover member 60.

The Young's modulus of the cover member 60 is, for example, greater than the Young's modulus of the measurement site of the living body M. Therefore, when the measurement site of the living body M comes into contact with the cover member 60, the measurement site of the living body M is deformed according to the shape of the cover member 60. This makes it possible to eliminate an air layer between the measurement site of the living body M and the cover member 60. When an air layer is present between the living body M and the cover member 60 or between the detecting device 10 and the cover member 60, stray light or light loss occurs due to Fresnel reflection.

1.3. Actions and Effects

The detecting device 10 includes the flexible substrate 40, the light-emitting unit 20 provided on the flexible substrate 40 and configured to emit light toward the living body M, and the light-receiving unit 30 provided on the flexible substrate 40 and configured to receive light from the living body M based on the light emitted from the light-emitting unit 20. The light-emitting unit 20 is constituted by a flexible organic light-emitting diode, and the light-receiving unit 30 is constituted by a flexible organic photodetector.

Therefore, in the detecting device 10, it is possible to prevent an air layer from being present between the light-emitting unit 20 and the cover member 60 and between the light-receiving unit 30 and the cover member 60 without providing a layer that curves in accordance with the shape of the cover member 60 between the light-emitting unit 20 and the cover member 60 and between the light-receiving unit 30 and the cover member 60. When the detecting device 10 is directly adhered to the living body M without using the cover member 60, it is possible to prevent an air layer from being present between the light-emitting unit 20 and the living body M and between the light-receiving unit 30 and the living body M even if a layer that curves in accordance with a shape of the living body M is not provided between the light-emitting unit 20 and the living body M and between the light-receiving unit 30 and the living body M. Accordingly, a distance between the light-emitting unit 20 and the living body M and a distance between the light-receiving unit 30 and the living body M can be reduced compared to a case in which a curved layer is provided. As a result, the amount of light received by the light-receiving unit 30 can be increased.

The detecting device 10 is adhered to the cover member 60 that comes into contact with the living body M, the light exiting from the light-emitting unit 20 passes through the cover member 60 and is incident on the living body M, and the light-emitting unit 20, the light-receiving unit 30, and the flexible substrate 40 can be deformed in accordance with the shape of the cover member 60.

Therefore, the detecting device 10 can be adhered to the cover member 60 without an air layer present between the detecting device 10 and the cover member 60. Accordingly, the measurement site of the living body M is not limited.

2. Modified Examples of Detecting Device

2.1. First Modified Example

Figure 5:
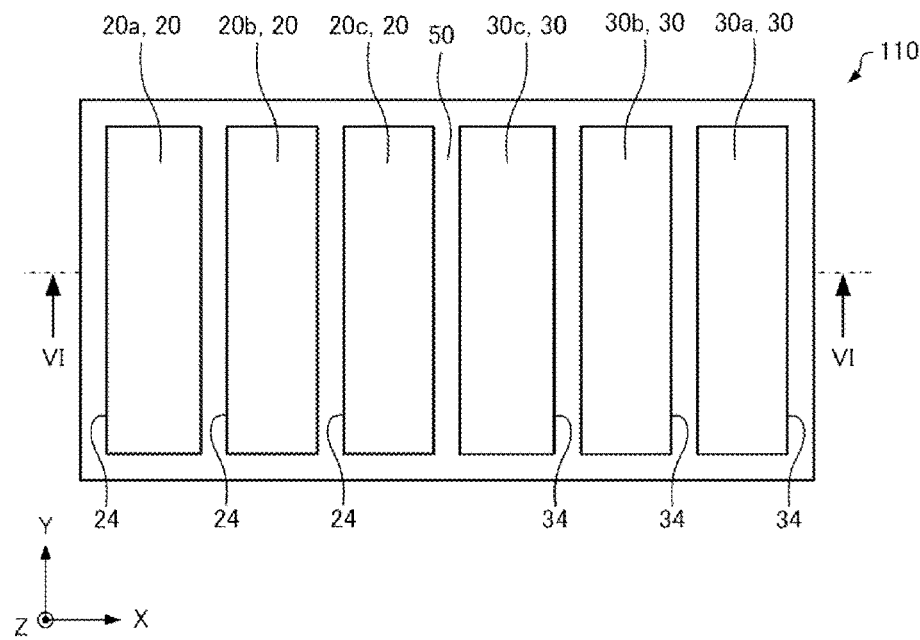
FIG. 5 is a plan view schematically illustrating a detecting device according to a first modified example of the exemplary embodiment.
Figure 6:
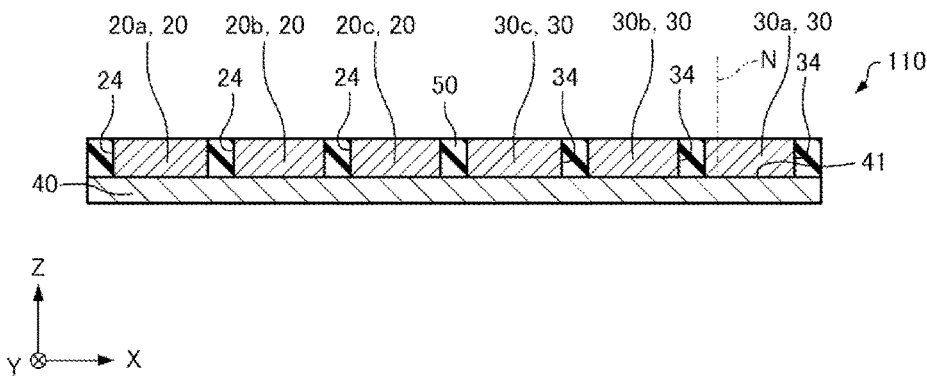
FIG. 6 is a cross-sectional view schematically illustrating the detecting device according to the first modified example of the exemplary embodiment.
Figure 7:
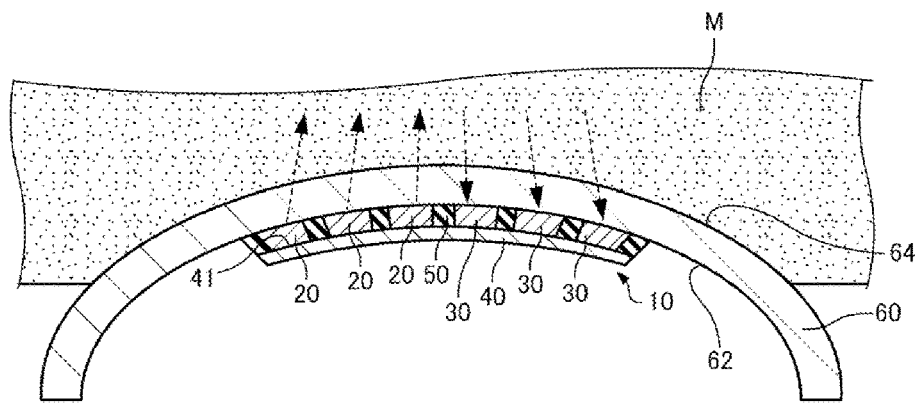
FIG. 7 is a cross-sectional view schematically illustrating a usage state of the detecting device according to the first modified example of the exemplary embodiment.
Figure 8:
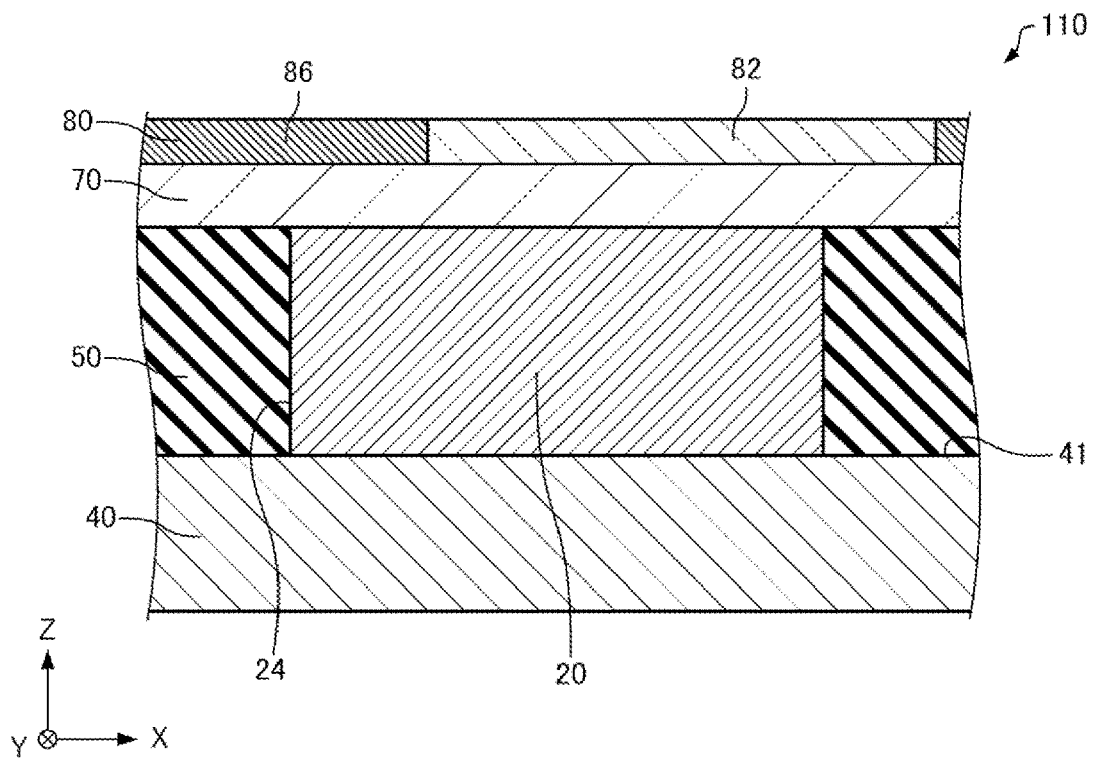
FIG. 8 is a cross-sectional view schematically illustrating the detecting device according to the first modified example of the exemplary embodiment.
Figure 9:
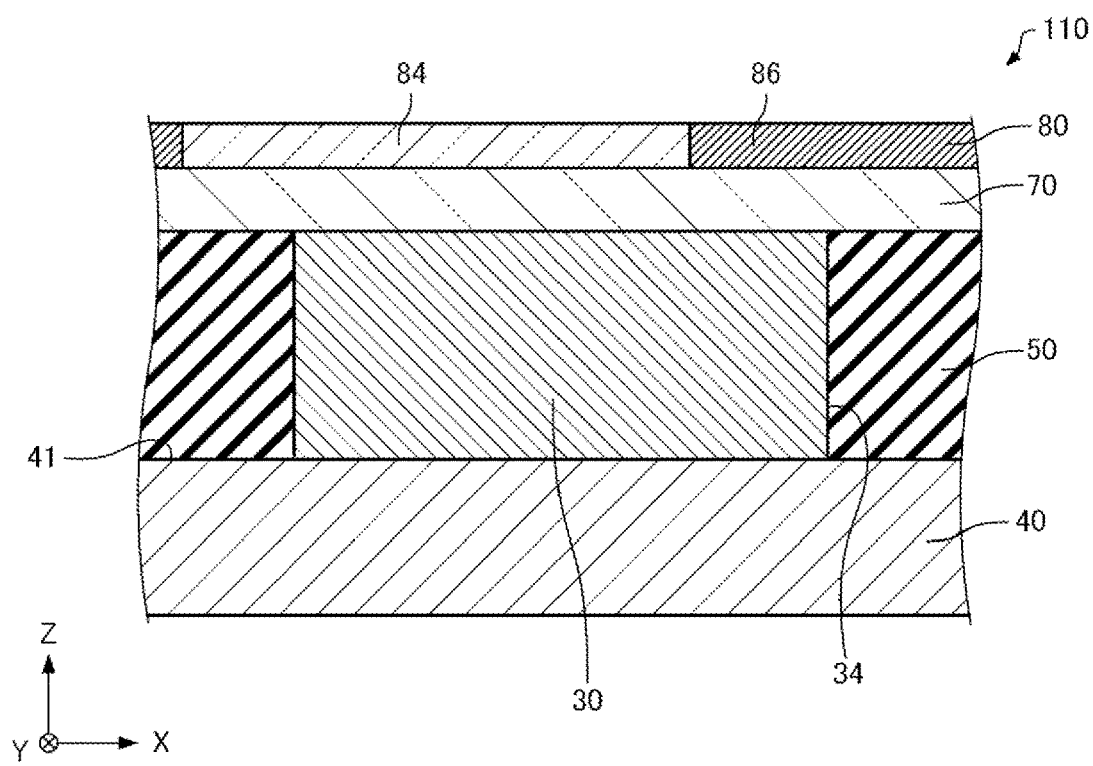
FIG. 9 is a cross-sectional view schematically illustrating the detecting device according to the first modified example of the exemplary embodiment.

Next, a detecting device according to a first modified example of this exemplary embodiment will be described with reference to the accompanying drawings. FIG. 5 is a plan view schematically illustrating a detecting device 110 according to the first modified example of the exemplary embodiment. FIG. 6 is a cross-sectional view taken along line VI-VI of FIG. 5, schematically illustrating the detecting device 110 according to the first modified example of the exemplary embodiment. FIG. 7 is a cross-sectional view schematically illustrating a usage state of the detecting device 110 according to the first modified example of the exemplary embodiment. FIG. 8 and FIG. 9 are each an enlarged cross-sectional view schematically illustrating a portion of the detecting device 110 according to the first modified example of the exemplary embodiment.

Note that FIGS. 5, 6, 8, and 9 each illustrate a state in which the detecting device 110 is not adhered to the cover member 60. FIG. 7 illustrates a state in which the detecting device 110 is adhered to the cover member 60.

Hereinafter, in the detecting device 110 according to the first modified example of the exemplary embodiment, members having the same functions as those of the constituent members of the detecting device 10 according to the exemplary embodiment described above are denoted by the same reference signs, and detailed description thereof will be omitted. The same applies to detecting devices according to second and third modified examples of the exemplary embodiment described below.

As illustrated in FIG. 8 and FIG. 9, the detecting device 110 is different from the detecting device 10 described above in including a sealing layer 70 and an angle-limiting filter 80. Note that, for the sake of convenience, the sealing layer 70 and the angle-limiting filter 80 are not illustrated in FIG. 5 to FIG. 7.

As illustrated in FIG. 8 and FIG. 9, the sealing layer 70 covers the light-emitting surface, the light-receiving surface, the light-emitting unit 20, and the light-receiving unit 30. The sealing layer 70 seals the light-emitting unit 20 and the light-receiving unit 30. In the illustrated example, the sealing layer 70 is provided on the light-emitting unit 20, the light-receiving unit 30, and the spacer member 50.

The sealing layer 70 has light transmissivity. The sealing layer 70 transmits the light exiting from the light-emitting unit 20. The sealing layer 70 transmits light from the living body M. The sealing layer 70 is a flexible layer. A material of the sealing layer 70 is, for example, $SiO_2$, SiON, SiN, or $Al_2O_3$.

The angle-limiting filter 80 is provided on the sealing layer 70. The angle-limiting filter 80 includes, for example, an exiting light transmission filter 82, an incident light transmission filter 84, and a light-blocking filter 86.

The exiting light transmission filter 82 transmits light exiting from the light-emitting unit 20. In the illustrated example, when viewed from the Z-axis direction, a portion of the exiting light transmission filter 82 overlaps the light-emitting unit 20. The incident light transmission filter 84 transmits light from the living body M. In the illustrated example, when viewed from the Z-axis direction, a portion of the incident light transmission filter 84 overlaps the light-receiving unit 30. The transmission filters 82, 84 may be color filters corresponding to the wavelength of the light exiting from the light-emitting unit 20. The transmission filters 82, 84 are flexible filters. A material of the transmission filters 82, 84 is, for example, an acrylic resin mixed with a pigment.

The light-blocking filter 86 is provided in the sealing layer 70. The light-blocking filter 86 is in contact with the transmission filters 82, 84. When viewed from the Z-axis direction, the light-blocking filter 86 surrounds the transmission filters 82, 84.

The light-blocking filter 86 blocks light exiting from the light-emitting unit 20. The light-blocking filter 86 blocks light traveling toward the light-receiving unit 30. In the illustrated example, when viewed from the Z-axis direction, an end portion 24 of the light-emitting unit 20 on the side opposite to the light-receiving unit 30 overlaps the light-blocking filter 86. The end portion 24 is an end portion of the light-emitting unit 20 in the −X-axis direction. When viewed from the Z-axis direction, an end portion 34 of the light-receiving unit 30 on the side opposite to the light-emitting unit 20 overlaps the light-blocking filter 86. The end portion 34 is an end portion of the light-receiving unit 30 in the +X-axis direction. The light-blocking filter 86 is a flexible filter. A material of the light-blocking filter 86 is, for example, an acrylic resin mixed with a pigment.

As illustrated in FIG. 5 to FIG. 7, the detecting device 110 includes, for example, a plurality of the light-emitting units 20. In the illustrated example, three light-emitting units 20a, 20b, 20c are provided as the plurality of light-emitting units 20. In the example illustrated in FIG. 5, shapes of the light-emitting units 20a, 20b, 20c are rectangles having long sides parallel to the Y-axis. In the illustrated example, the light-emitting units 20a, 20b, 20c are aligned in the X-axis direction. The light-emitting unit 20b is provided between the light-emitting unit 20a and the light-emitting unit 20c. The light-emitting unit 20c is provided between the light-receiving unit 30 and the light-emitting unit 20b. The light-emitting unit 20 and the light-receiving unit 30 do not deform in the Y-axis direction, but can be deformed into a curved shape bent into an arc in the X-axis direction.

The detecting device 110 includes, for example, a plurality of the light-receiving units 30. In the illustrated example, three light-receiving units 30a, 30b, 30c are provided as the plurality of light-receiving units 30. In the example illustrated in FIG. 5, shapes of the light-receiving units 30a, 30b, 30c are rectangles having long sides parallel to the Y-axis. In the illustrated example, the light-receiving units 30a, 30b, 30c are aligned in the X-axis direction. The light-receiving unit 30b is provided between the light-receiving unit 30a and the light-receiving unit 30c. The light-receiving unit 30c is provided between the light-emitting unit 20 and the light-receiving unit 30b.

A distance between the light-emitting unit 20a and the light-receiving unit 30c is greater than a distance between the light-emitting unit 20b and the light-receiving unit 30c. The distance between the light-emitting unit 20b and the light-receiving unit 30c is greater than a distance between the light-emitting unit 20c and the light-receiving unit 30c.

A distance between the light-receiving unit 30a and the light-emitting unit 20c is greater than a distance between the light-receiving unit 30b and the light-emitting unit 20c. The distance between the light-receiving unit 30b and the light-emitting unit 20c is greater than the distance between the light-receiving unit 30c and the light-emitting unit 20c.

Figure 10:
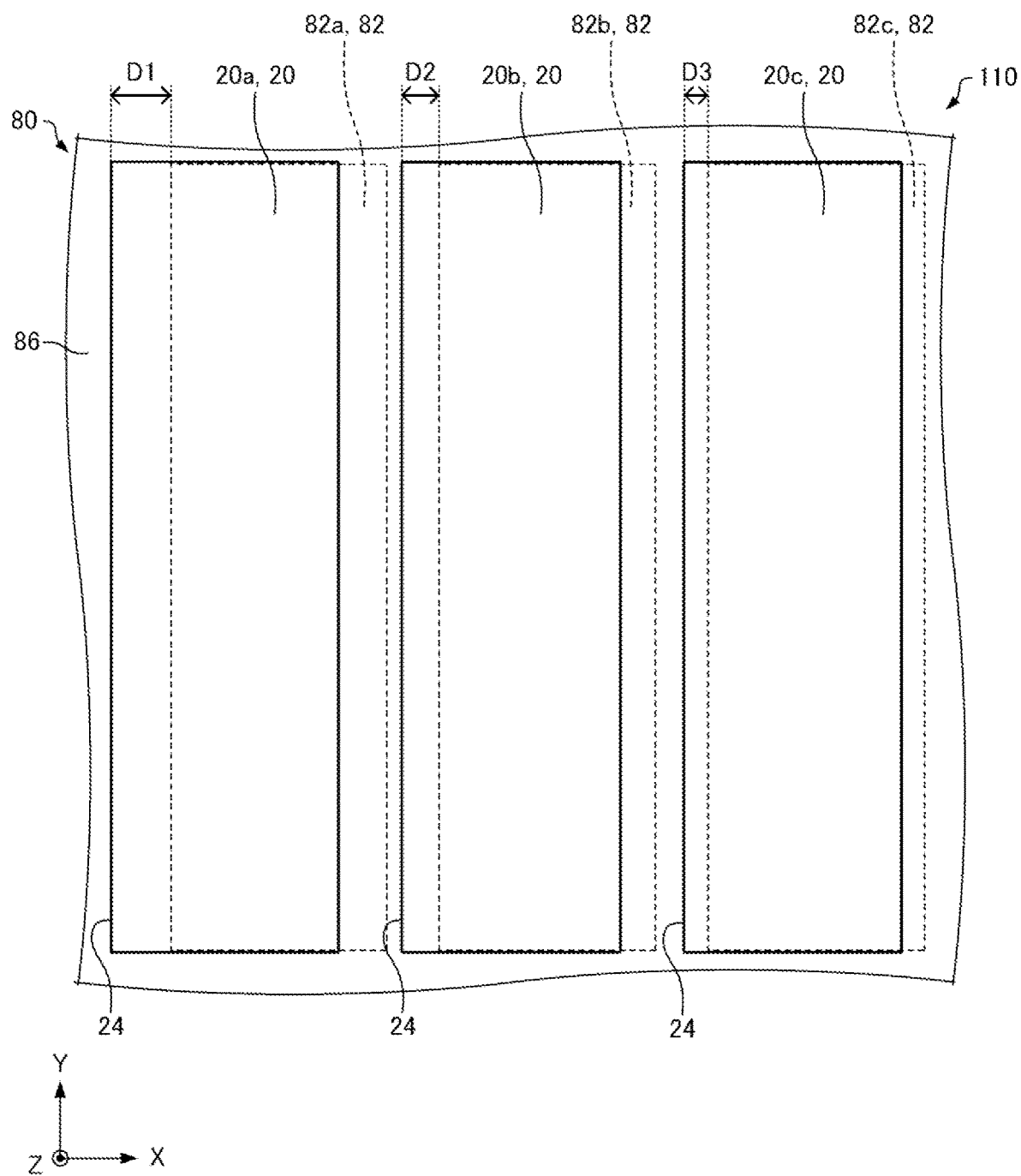
FIG. 10 is a plan view schematically illustrating the detecting device according to the first modified example of the exemplary embodiment.
Figure 11:
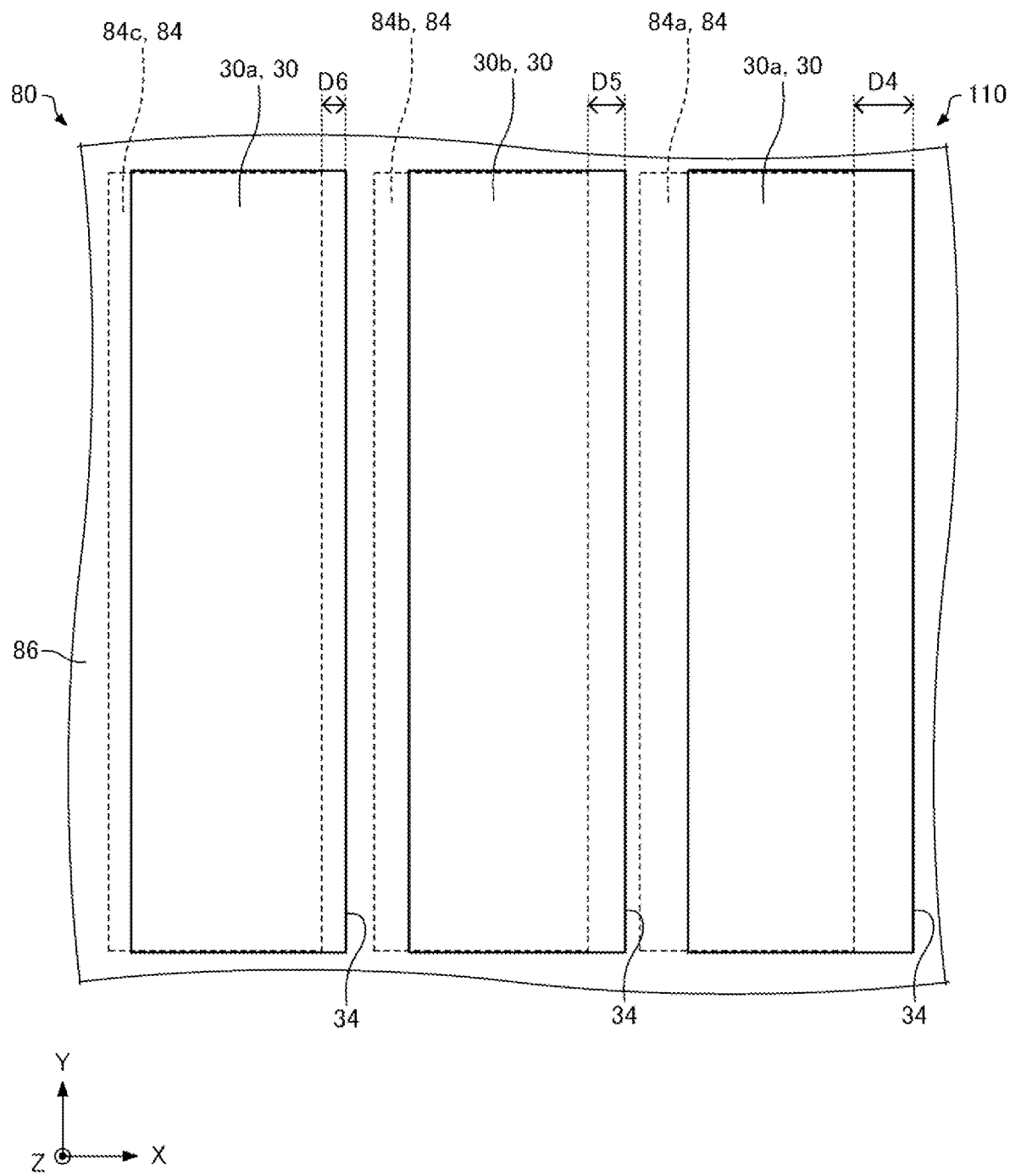
FIG. 11 is a plan view schematically illustrating the detecting device according to the first modified example of the exemplary embodiment.

FIG. 10 and FIG. 11 are plan views schematically illustrating the detecting device 110. Note that FIG. 10 and FIG. 11 illustrate a state in which the detecting device 110 is not adhered to the cover member 60. Further, for the sake of convenience, members other than the light-emitting unit 20 and the angle-limiting filter 80 are not illustrated in FIG. 10. In FIG. 10, the exiting light transmission filter 82 of the angle-limiting filter 80 is indicated by a dashed line. Further, members other than the light-receiving unit 10 and the angle-limiting filter 80 are not illustrated in FIG. 11. In FIG.

11, the incident light transmission filter 84 of the angle-limiting filter 80 is indicated by a dashed line.

As illustrated in FIG. 10, a plurality of the exiting light transmission filters 82 are provided correspondingly to the number of light-emitting units 20. In the illustrated example, three exiting light transmission filters 82*a*, 82*b*, 82*c* are provided as the plurality of exiting light transmission filters 82. Shapes of the exiting light transmission filters 82*a*, 82*b*, 82*c* are rectangles having long sides parallel to the Y-axis. When viewed from the Z-axis direction, a portion of the exiting light transmission filter 82*a* overlaps the light-emitting unit 20*a*. A portion of the exiting light transmission filter 82*b* overlaps the light-emitting unit 20*b*. A portion of the exiting light transmission filter 82*c* overlaps the light-emitting unit 20*c*.

When viewed from the Z-axis direction, a distance D1 is greater than a distance D2. The distance D2 is greater than a distance D3. The distance D1 is a distance between the end portion 24 of the light-emitting unit 20*a* and a boundary between the exiting light transmission filter 82*a* and the light-blocking filter 86. The distance D2 is a distance between the end portion 24 of the light-emitting unit 20*b* and a boundary between the exiting light transmission filter 82*b* and the light-blocking filter 86. The distance D3 is a distance between the end portion 24 of the light-emitting unit 20*c* and a boundary between the exiting light transmission filter 82*c* and the light-blocking filter 86.

Thus, in the detecting device 110, the farther the light-emitting unit 20 is from the light-receiving unit 30, the greater the distance is between the end portion 24 of the light-emitting unit 20 and the boundary between the exiting light transmission filter 82 and the light-blocking filter 86.

As illustrated in FIG. 11, a plurality of the incident light transmission filters 84 are provided correspondingly to the number of the light-receiving units 30. In the illustrated example, three incident light transmission filters 84*a*, 84*b*, 84*c* are provided as the plurality of incident light transmission filters 84. Shapes of the incident light transmission filters 84*a*, 84*b*, 84*c* are rectangles having long sides parallel to the Y-axis. When viewed from the Z-axis direction, a portion of the incident light transmission filter 84*a* overlaps the light-receiving unit 30*a*. A portion of the incident light transmission filter 84*b* overlaps the light-receiving unit 30*b*. A portion of the incident light transmission filter 84*c* overlaps the light-receiving unit 30*c*.

When viewed from the Z-axis direction, a distance D4 is greater than a distance D5. The distance D5 is greater than a distance D6. The distance D4 is a distance between the end portion 34 of the light-receiving unit 30*a* and a boundary between the incident light transmission filter 84*a* and the light-blocking filter 86. The distance D5 is a distance between the end portion 34 of the light-receiving unit 30*b* and a boundary between the incident light transmission filter 84*b* and the light-blocking filter 86. The distance D6 is a distance between the end portion 34 of the light-receiving unit 30*c* and a boundary between the incident light transmission filter 84*c* and the light-blocking filter 86.

Thus, in the detecting device 110, the farther the light-receiving unit 30 is from the light-emitting unit 20, the greater the distance is between the end portion 34 of the light-receiving unit 30 and the boundary between the incident light transmission filter 84 and the light-blocking filter 86.

The detecting device 110 includes the light-blocking filter 86 serving as a first light-blocking filter that blocks the light exiting from the light-emitting unit 20, the cover member 60 includes the first surface 62 onto which the detecting device 110 is adhered and the second surface 64 that comes into contact with the living body M and is on a side opposite to the first surface 62, and the cover member 60 has a convex shape in which the first surface 62 faces inward and the second surface 64 faces outward. In a state in which the detecting device 110 is not adhered to the cover member 60, the end portion 24 of the light-emitting unit 20 on the side opposite to the light-receiving unit 30 overlaps the light-blocking filter 86 when viewed from the normal N direction of the flexible substrate 40.

Therefore, in the detecting device 110, light exiting from the light-emitting unit 20 and not incident on the light-receiving unit 30 can be blocked by the light-blocking filter 86. Accordingly, stray light can be reduced. When the shape of the cover member 60 is convex, the light exiting from the end portion 24 of the light-emitting unit 20 is not directed toward the light-receiving unit 30 side, and thus, in consideration of reducing stray light, it is preferable to block the light before incidence on the living body M.

The detecting device 110 includes the light-blocking filter 86 as a second light-blocking filter that blocks light traveling toward the light-receiving unit 30 and, in a state in which the detecting device 110 is not adhered to the cover member 60, the end portion 34 of the light-receiving unit 30 on a side opposite to the light-emitting unit 20 overlaps the light-blocking filter 86 when viewed from the normal N direction of the flexible substrate 40.

Therefore, in the detecting device 110, light that is not from the living body M can be blocked by the light-blocking filter 86. Thus, the light-receiving unit 30 may have a high signal-to-noise ratio (SN ratio). Accordingly, the light-receiving unit 30 can receive the light from the living body M with high accuracy, making it possible to suppress the amount of light emitted from the light-emitting unit 20. Accordingly, power consumption can be reduced. Examples of light that is not light from the living body M include sunlight and light from a fluorescent lamp in a room in which the detecting device 110 is disposed.

In the detecting device 110, the farther the light-emitting unit 20 is from the light-receiving unit 30, the greater the distance is between the end portion 24 of the light-emitting unit 20 and the boundary between the exiting light transmission filter 82 and the light-blocking filter 86. Therefore, light exiting from the light-emitting unit 20 and not incident on the light-receiving unit 30 can be more reliably blocked by the light-blocking filter 86.

In the detecting device 110, the farther the light-receiving unit 30 is from the light-emitting unit 20, the greater the distance is between the end portion 34 of the light-receiving unit 30 and the boundary between the incident light transmission filter 84 and the light-blocking filter 86. Therefore, light that is not light from the living body M can be more reliably blocked by the light-blocking filter 86.

Note that, in the example described above, the light-blocking filter 86 is a common light-blocking filter that functions as both a first light-blocking filter that blocks light exiting from the light-emitting unit 20 and a second filter that blocks light traveling toward the light-receiving unit 30. Although not illustrated, the first light-blocking filter and the second light-blocking filter may be separate light-blocking filters.

Further, in the example described above, the cover member 60 has a convex shape in which the first surface 62 faces inward and the second surface 64 faces outward. Although not illustrated, the cover member 60 may have a concave shape in which the first surface 62 faces outward and the second surface 64 faces inward. In this case, when viewed from the Z-axis direction, the light-blocking filter 86 overlaps the end portion of the light-emitting unit 20 on the light-receiving unit 30 side, and further overlaps the end portion of the light-receiving unit 30 on the light-emitting unit 20 side.

Further, the light-emitting unit 20 and the light-receiving unit 30 are flexible, eliminating the need to increase thicknesses of the flexible sealing layer 70 and filters 82, 84, 86 for the purpose of eliminating the air layer between the light-emitting unit 20 and the cover member 60 and the air layer between the light-receiving unit 30 and the cover member 60, for example. This makes it possible to reduce the thicknesses of the sealing layer 70 and the filters 82, 84, 86 compared to a case in which a sealing layer or a filter is provided covering a light-emitting unit and a light-receiving unit which are not flexible, for example.

2.2. Second Modified Example

Figure 12:
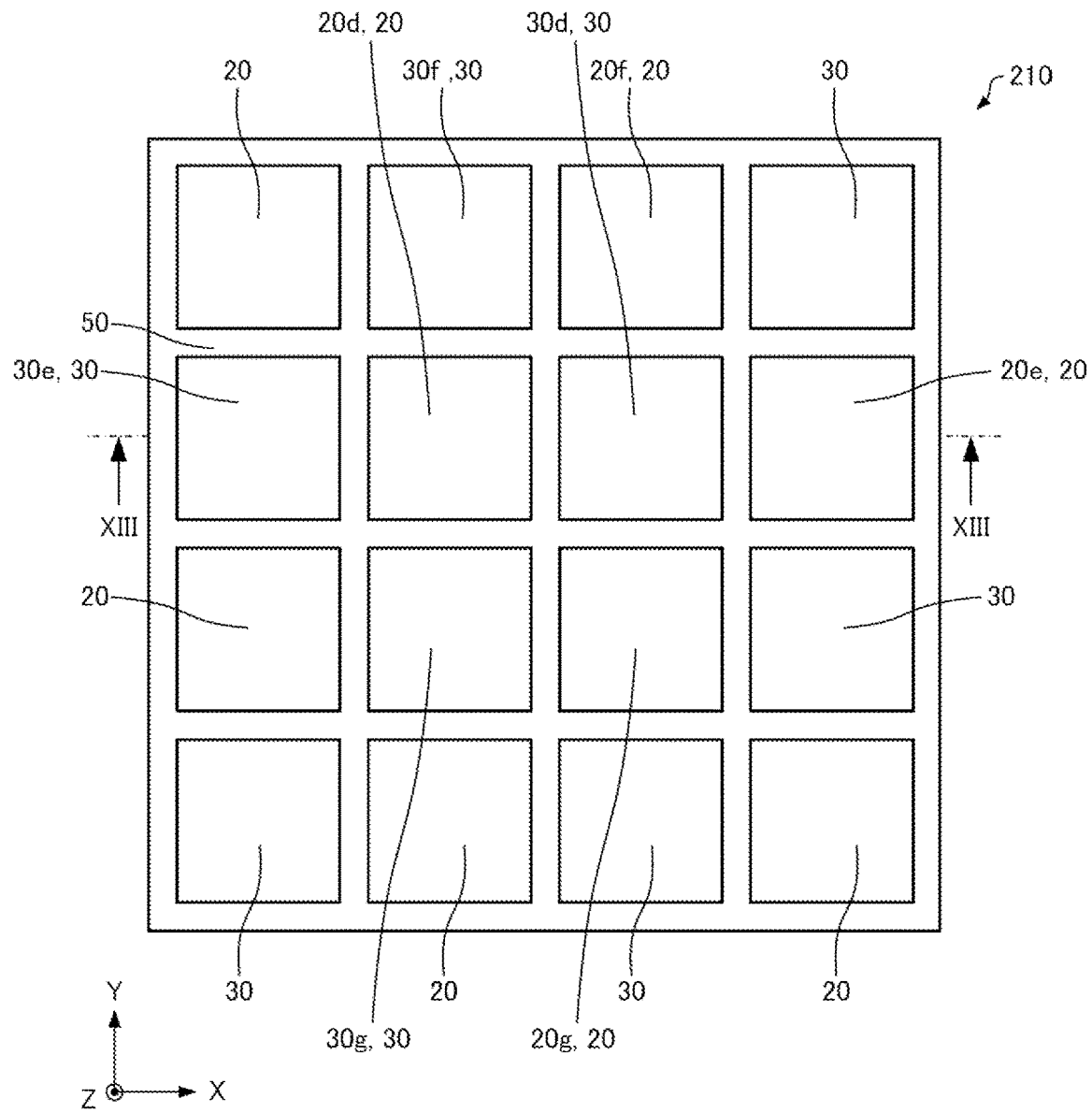
FIG. 12 is a plan view schematically illustrating a detecting device according to a second modified example of the exemplary embodiment.
Figure 13:
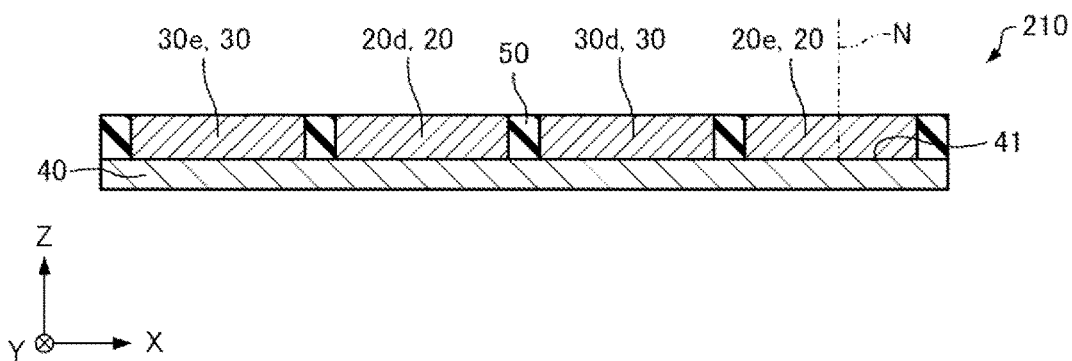
FIG. 13 is a cross-sectional view schematically illustrating the detecting device according to the second modified example of the exemplary embodiment.
Figure 14:
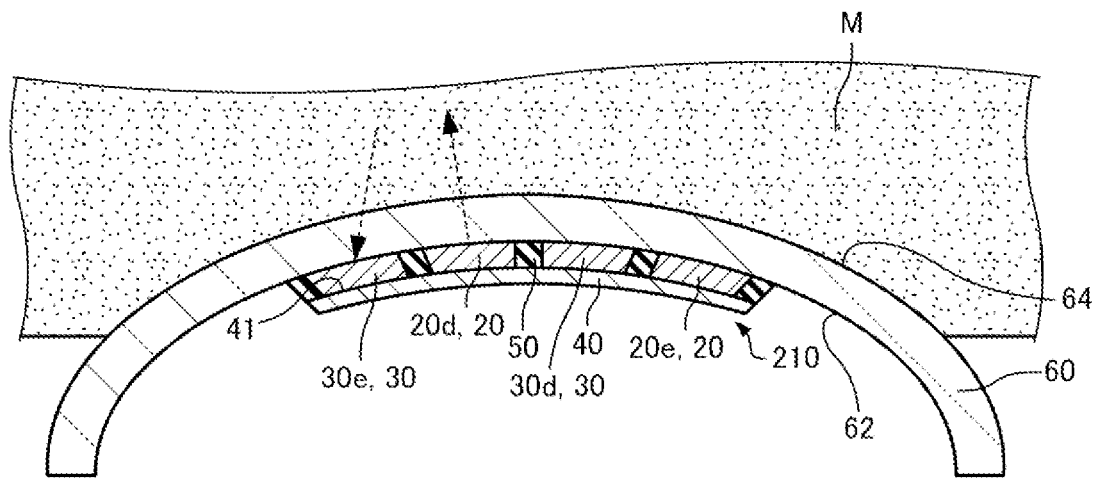
FIG. 14 is a cross-sectional view schematically illustrating a usage state of the detecting device according to the second modified example of the exemplary embodiment.
Figure 15:
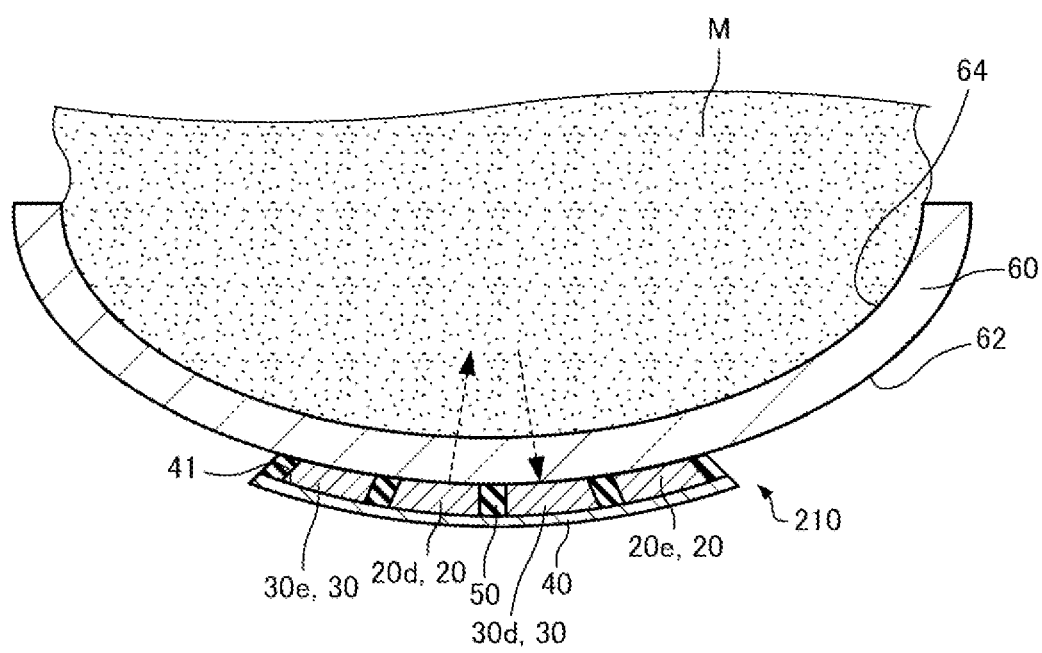
FIG. 15 is a cross-sectional view schematically illustrating a usage state of the detecting device according to the second modified example of the exemplary embodiment.

Next, a detecting device according to a second modified example of this exemplary embodiment will be described with reference to the accompanying drawings. FIG. 12 is a plan view schematically illustrating a detecting device 210 according to the second modified example of the exemplary embodiment. FIG. 13 is a cross-sectional view taken along line XIII-XIII of FIG. 12, schematically illustrating the detecting device 210 according to the second modified example of the exemplary embodiment. FIG. 14 and FIG. 15 are each a cross-sectional view schematically illustrating a usage state of the detecting device 210 according to the second modified example of the exemplary embodiment.

Note that FIG. 12 and FIG. 13 illustrate a state in which the detecting device 210 is not adhered to the cover member 60. FIG. 14 and FIG. 15 illustrate a state in which the detecting device 210 is adhered to the cover member 60.

As illustrated in FIG. 12 and FIG. 13, the detecting device 210 is different from the detecting device 10 described above in including a plurality of the light-emitting units 20 and a plurality of the light-receiving units 30.

As illustrated in FIG. 12, the plurality of light-emitting units 20 and the plurality of light-receiving units 30 are arrayed in a matrix in the X-axis direction and the Y-axis direction when viewed from the Z-axis direction. The light-emitting units 20 and the light-receiving units 30 are alternately arrayed in the X-axis direction. The light-emitting units 20 and the light-receiving units 30 are alternately arrayed in the Y-axis direction.

When viewed from the Z-axis direction, among the plurality of light-emitting units 20, a light-emitting unit 20d and a light-emitting unit 20e are aligned in the first direction on the main surface 41 of the flexible substrate 40. In the illustrated example, the first direction is the X-axis direction. Among the plurality of light-emitting units 20, a light-emitting unit 20f and a light-emitting unit 20g are aligned in a second direction intersecting the first direction. In the illustrated example, the second direction is a direction orthogonal to the first direction and is the Y-axis direction. The light-emitting unit 20d and the light-emitting unit 20e are light-emitting units 20 adjacent to each other in the X-axis direction. The light-emitting unit 20f and the light-emitting unit 20g are light-emitting units 20 adjacent to each other in the Y-axis direction.

When viewed from the Z-axis direction, among the plurality of light-receiving units 30, a light-receiving unit 30d and a light-receiving unit 30e are aligned in the X-axis direction. Among the plurality of light-receiving units 30, a light-receiving unit 30f and a light-receiving unit 30g are aligned in the Y-axis direction. The light-receiving unit 30d and the light-receiving unit 30e are light-receiving units 30 adjacent to each other in the X-axis direction. The light-receiving unit 30f and the light-receiving unit 30g are light-receiving units 30 adjacent to each other in the Y-axis direction.

When viewed from the Z-axis direction, the light-emitting unit 20d is provided between the light-receiving unit 30d and the light-receiving unit 30e. Furthermore, the light-emitting unit 20d is provided between the light-receiving unit 30f and the light-receiving unit 30g. The light-receiving unit 30d is provided between the light-emitting unit 20d and the light-emitting unit 20e. Furthermore, the light-receiving unit 30d is provided between the light-emitting unit 20f and the light-emitting unit 20g.

In the detecting device 210, when viewed from the normal N direction of the flexible substrate 40, the light-receiving unit 30d as a first light-receiving unit and the light-receiving unit 30e as a second light-receiving unit are aligned in the first direction, the light-receiving unit 30f as a third light-receiving unit and the light-receiving unit 30g as a fourth light-receiving unit are aligned in the second direction intersecting with the first direction, and the light-emitting unit 20d as a first light-emitting unit is provided between the light-receiving unit 30d and the light-receiving unit 30e and between the light-receiving unit 30f and the light-receiving unit 30g.

Therefore, in the detecting device 210, as illustrated in FIG. 14, when the shape of the cover member 60 is a convex shape in which the first surface 62 faces inward and the second surface 64 faces outward, the light from the living body M based on the light exiting from the light-emitting unit 20d is received by the light-receiving unit 30e. As illustrated in FIG. 15, when the shape of the cover member 60 is a concave shape in which the first surface 62 faces outward and the second surface 64 faces inward, the light from the living body M based on the light exiting from the light-emitting unit 20d is received by the light-receiving unit 30d.

Thus, in the detecting device 210, whether the shape of the cover member 60 is convex or concave, the light from the living body M based on the light exiting from the light-emitting unit 20d can be received, regardless of the shape of the detecting device 210 in the usage state.

In the detecting device 210, on the main surface 41 of the flexible substrate 40, the light-emitting unit 20d as the first light-emitting unit and the light-emitting unit 20e as a second light-emitting unit are aligned in the first direction, the light-emitting unit 20f as a third light-emitting unit and the light-emitting unit 20g as a fourth light-emitting unit are aligned in the second direction, and the light-receiving unit 30d as the first light-receiving unit is provided between the light-emitting unit 20d and the light-emitting unit 20e and between the light-emitting unit 20f and the light-emitting unit 20g.

Thus, in the detecting device 210, whether the shape of the cover member 60 is convex or concave, the light-receiving unit 30d can receive the light from the living body M based on the light exiting from at least one of the light-emitting units 20d, 20e, 20f, 20g, regardless of the shape of the detecting device 210 in the usage state.

2.3. Third Modified Example

Figure 16:
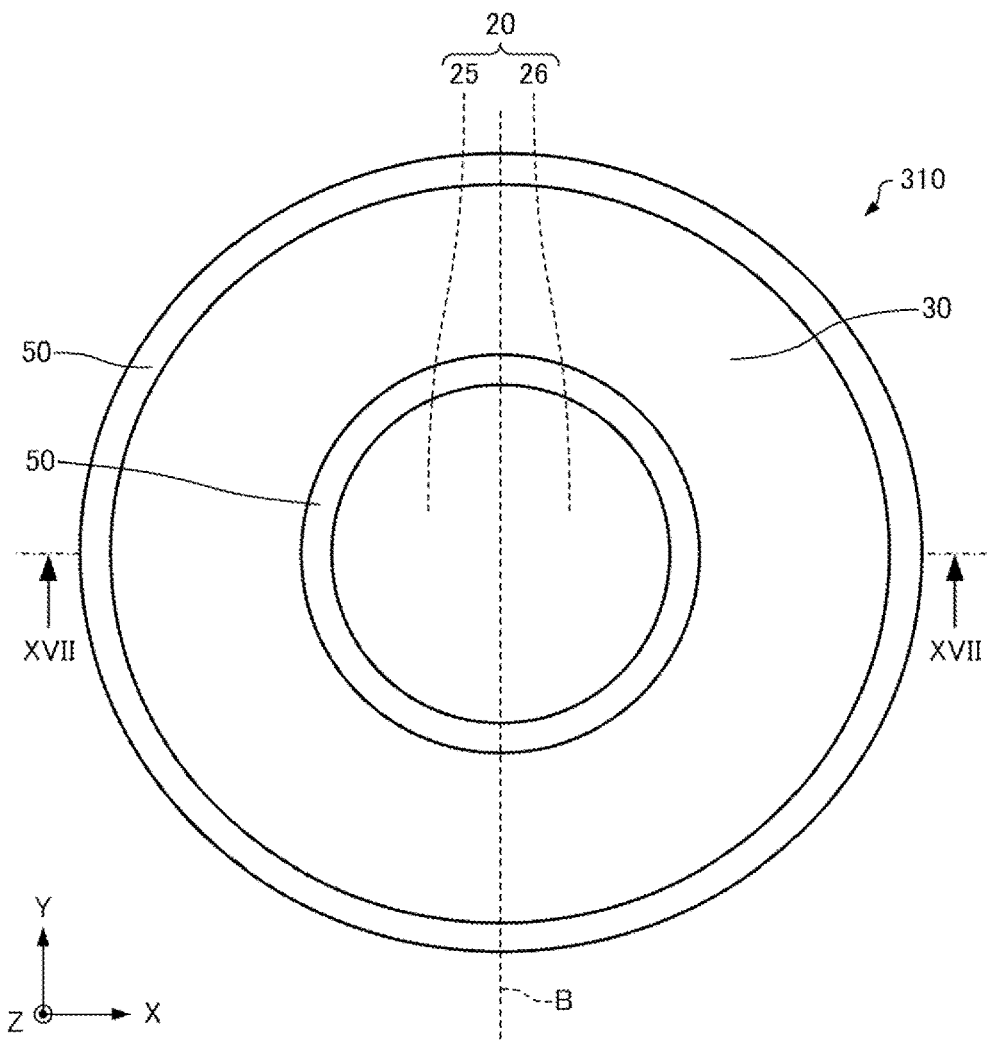
FIG. 16 is a plan view schematically illustrating a detecting device according to a third modified example of the exemplary embodiment.
Figure 17:
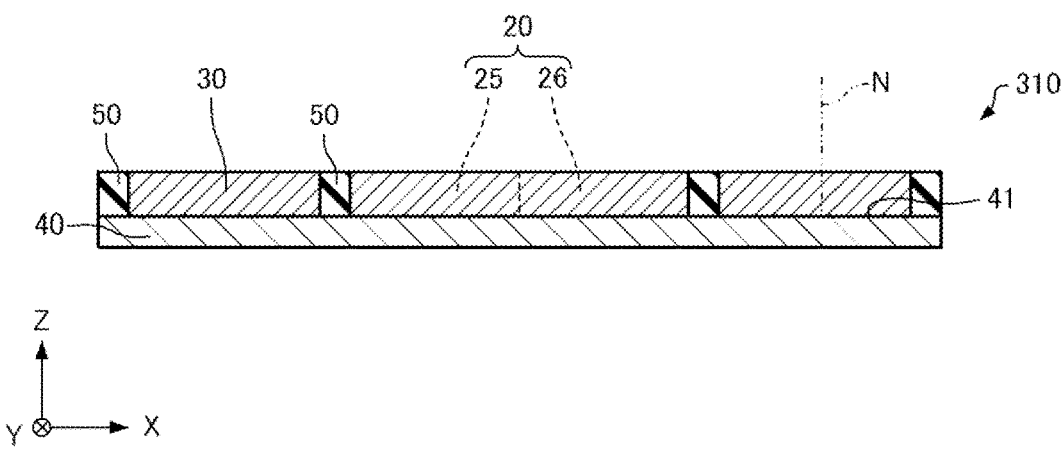
FIG. 17 is a cross-sectional view schematically illustrating the detecting device according to the third modified example of the exemplary embodiment.
Figure 18:
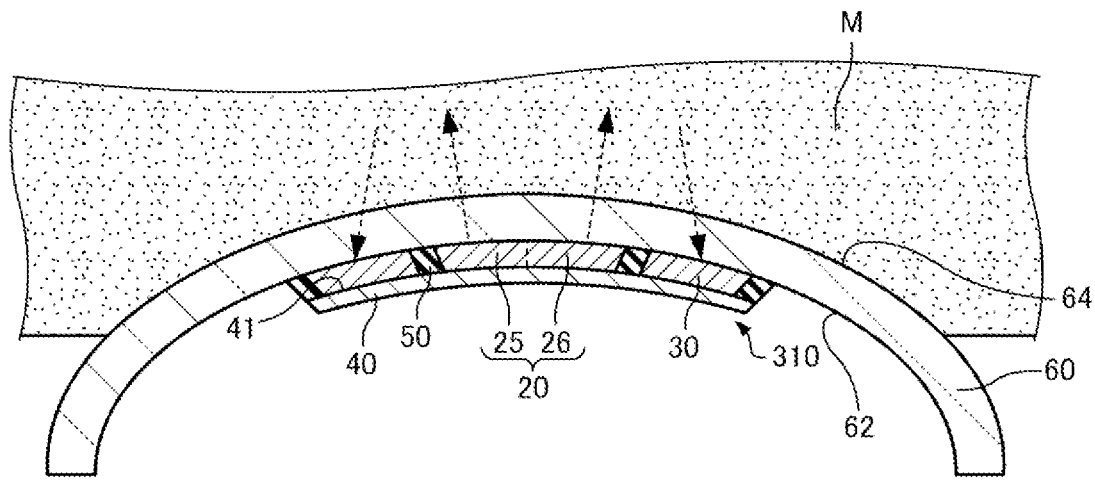
FIG. 18 is a cross-sectional view schematically illustrating a usage state of the detecting device according to the third modified example of the exemplary embodiment.
Figure 19:
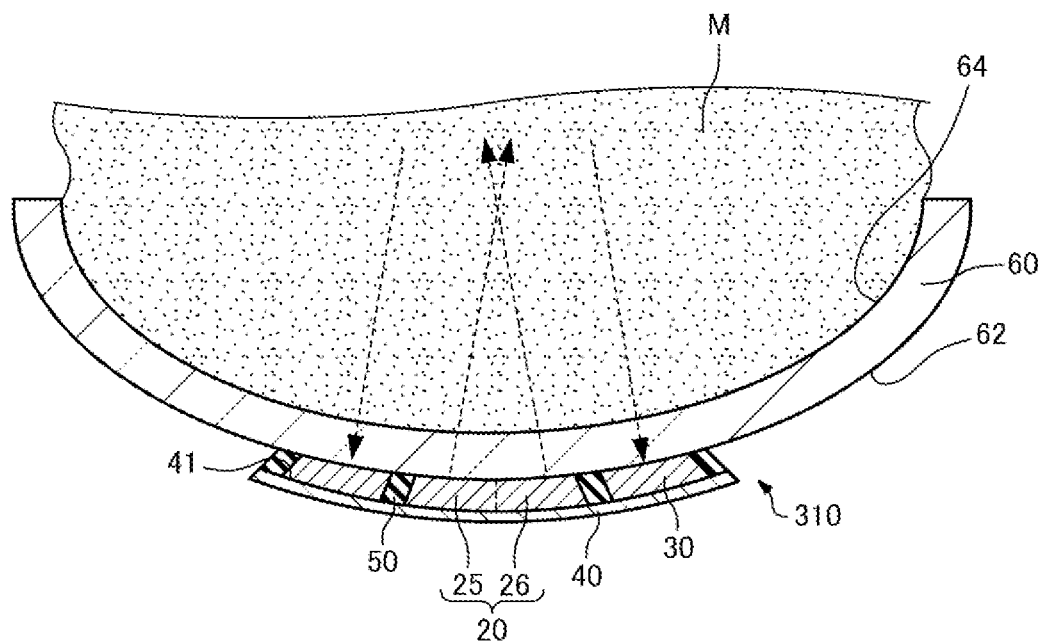
FIG. 19 is a cross-sectional view schematically illustrating a usage state of the detecting device according to the third modified example of the exemplary embodiment.

Next, a detecting device according to a third modified example of this exemplary embodiment will be described with reference to the accompanying drawings. FIG. 16 is a plan view schematically illustrating a detecting device 310 according to the third modified example of the exemplary embodiment. FIG. 17 is a cross-sectional view taken along line XVII-XVII of FIG. 16, schematically illustrating the detecting device 310 according to the third modified example of the exemplary embodiment. FIG. 18 and FIG. 19 are each a cross-sectional view schematically illustrating a usage state of the detecting device 310 according to the third modified example of the exemplary embodiment.

Note that FIG. 16 and FIG. 17 illustrate a state in which the detecting device 310 is not adhered to the cover member 60. FIG. 18 and FIG. 19 illustrate a state in which the detecting device 310 is adhered to the cover member 60.

As illustrated in FIG. 16 and FIG. 17, the detecting device 310 is different from the detecting device 10 described above in that the light-receiving unit 30 surrounds the light-emitting unit 20 on the main surface 41 of the flexible substrate 40 when viewed from the Z-axis direction.

In the example illustrated in FIG. 16, the shape of light-emitting unit 20 is circular when viewed from the Z-axis direction. The shape of the light-receiving unit 30 is a ring when viewed from the Z-axis direction. When viewed from the Z-axis direction, a center and a position of the light-emitting unit 20 are the same as a center and a position of the light-receiving unit 30.

As illustrated in FIG. 17, when viewed from the Z-axis direction, the light-emitting unit 20 includes a first side portion 25 positioned on one side of a virtual straight line B, and a second side portion 26 positioned on the other side of the virtual straight line B. The virtual straight line B is a straight line passing through the center of the light-emitting unit 20 and parallel to the Y-axis. In the illustrated example, the first side portion 25 is positioned on the −X-axis direction side of the virtual straight line B. The second side portion 26 is positioned on the +X-axis direction side of the virtual straight line B.

In the detecting device 310, the light-receiving unit 30 surrounds the light-emitting unit 20 on the main surface 41 of the flexible substrate 40.

Therefore, in the detecting device 310, as illustrated in FIG. 18, when the shape of the cover member 60 is convex, the light exiting from the first side portion 25 of the light-emitting unit 20 is incident on the light-receiving unit 30 on the side closer to the first side portion 25. The light exiting from the second side portion 26 of the light-emitting unit 20 is incident on the light-receiving unit 30 on the side closer to the second side portion 26. As illustrated in FIG. 19, when the shape of the cover member 60 is concave, the light exiting from the first side portion 25 is incident on the light-receiving unit 30 closer to the second side portion 26. The light exiting from the second side portion 26 is incident on the light-receiving unit 30 on the side closer to the first side portion 25.

Thus, in the detecting device 310, whether the shape of the cover member 60 is convex or concave, the light from the living body M based on the light exiting from the light-emitting unit 20 can be received, regardless of the shape of the detecting device 310 in the usage state.

The exemplary embodiments and modified examples described above are merely examples, and the present disclosure is not limited thereto. For example, the exemplary embodiments and the modified examples may be combined as appropriate.

The present disclosure includes configurations that are substantially the same as the configurations described in the exemplary embodiments, such as, for example, configurations having the same function, method, and result or configurations having the same object and effect. The present disclosure also includes a configuration in which an unsubstantial portion described in the exemplary embodiments is replaced with another portion. The present disclosure also includes a configuration that achieves the same actions and effects, or a configuration capable of achieving the same object, as those of the configurations described in the exemplary embodiments. The present disclosure further includes a configuration obtained by adding a known technique to the configurations described in the exemplary embodiments.

The following contents are derived from the exemplary embodiments and modified examples described above.

A detecting device according to one aspect is a detecting device including a flexible substrate, a first light-emitting unit provided at the flexible substrate and configured to emit light toward a living body, and a first light-receiving unit provided at the flexible substrate and configured to receive light, based on the light exiting from the first light-emitting unit, from the living body. The first light-emitting unit is constituted by a flexible organic light-emitting diode, and the first light-receiving unit is constituted by a flexible organic photodetector.

According to this detecting device, it is possible to increase the amount of light received by the light-receiving unit.

In the detecting device according to one aspect, the detecting device may be adhered to a cover member that comes into contact with the living body, the light exiting from the first light-emitting unit may pass through the cover member and be incident on the living body, and the first light-emitting unit, the first light-receiving unit, and the flexible substrate may be configured to deform in accordance with a shape of the cover member.

According to this detecting device, the detecting device can be adhered to the cover member without an air layer present between the detecting device and the cover member.

The detecting device according to one aspect may include a first light-blocking filter configured to block the light exiting from the first light-emitting unit. The cover member may include a first surface onto which the detecting device is adhered and a second surface that comes into contact with the living body and is located on an opposite side from the first surface. The shape of the cover member may be a convex shape in which the first surface faces inward and the second surface faces outward. When viewed from a normal direction of the flexible substrate in a state in which the detecting device is not adhered to the cover member, an end portion on an opposite side of the first light-emitting unit from the first light-receiving unit may overlap the first light-blocking filter.

According to this detecting device, stray light can be reduced.

The detecting device according to one aspect may include a second light-blocking filter configured to block light traveling toward the first light-receiving unit. When viewed from the normal direction of the flexible substrate in a state in which the detecting device is not adhered to the cover member, an end portion on an opposite side of the first light-receiving unit from the first light-emitting unit may overlap the second light-blocking filter.

According to this detecting device, it is possible to block light that is not light from the living body based on the light exiting from the first light-emitting unit.

The detecting device according to one aspect may include a second light-receiving unit, a third light-receiving unit, and a fourth light-receiving unit provided at the flexible substrate and configured to receive light, based on the light exiting from the first light-emitting unit, from the living body. The second light-receiving unit, the third light-receiving unit, and the fourth light-receiving unit may each be constituted by a flexible organic photodetector. On a main surface of the flexible substrate, the first light-receiving unit and the second light-receiving unit may be aligned in a first direction, the third light-receiving unit and the fourth light-receiving unit may be aligned in a second direction intersecting the first direction, and the first light-emitting unit may be provided between the first light-receiving unit and the second light-receiving unit, and may be provided between the third light-receiving unit and the fourth light-receiving unit.

According to this detecting device, it is possible to receive the light from the living body based on the light exiting from the first light-emitting unit regardless of the shape of the detecting device in the usage state.

The detecting device according to one aspect may include a second light-emitting unit, a third light-emitting unit, and a fourth light-emitting unit provided at the flexible substrate and configured to emit light toward the living body. The second light-emitting unit, the third light-emitting unit, and the fourth light-emitting unit may each be constituted by a flexible organic light-emitting diode. On the main surface of the flexible substrate, the first light-emitting unit and the second light-emitting unit may be aligned in the first direction, the third light-emitting unit and the fourth light-emitting unit may be aligned in the second direction, and the first light-receiving unit may be provided between the first light-emitting unit and the second light-emitting unit, and may be provided between the third light-emitting unit and the fourth light-emitting unit.

According to this detecting device, regardless of the shape of the detecting device in the usage state, the first light-receiving unit can receive the light from the living body based on the light exiting from at least one of the first light-emitting unit, the second light-emitting unit, the third light-emitting unit, and the fourth light-emitting unit.

In the detecting device according to one aspect, the first light-emitting unit and the first light-receiving unit may be aligned in a first direction on the flexible substrate. When adhered to the living body, the detecting device may be deformed into a curved shape bent into an arc in the first direction.

In the detecting device according to one aspect, the first light-receiving unit may surround the first light-emitting unit on a main surface of the flexible substrate.

According to this detecting device, it is possible to receive the light from the living body based on the light exiting from the first light-emitting unit regardless of the shape of the detecting device in the usage state.

A measuring device according to an aspect includes the detecting device according to one aspect, and an information analysis unit configured to identify biological information from a detection signal indicating a detection result obtained by the detecting device.

What is claimed is:

1. A detecting device, comprising:
   a flexible substrate;
   a first light-emitting unit provided at the flexible substrate and configured to emit light toward a living body;
   a first light-receiving unit provided at the flexible substrate and configured to receive the light, based on the light exiting from the first light-emitting unit, from the living body; and
   a first light-blocking filter configured to block some of the light exiting from the first light-emitting unit, wherein
   the first light-emitting unit is constituted by a flexible organic light-emitting diode,
   the first light-receiving unit is constituted by a flexible organic photodetector,
   the detecting device is configured to be adhered to a cover member that comes into contact with the living body,
   the light exiting from the first light-emitting unit passes through the cover member and is incident on the living body,
   the first light-emitting unit, the first light-receiving unit, and the flexible substrate are configured to deform in accordance with a convex shape of the cover member,
   the detecting device is configured to be adhered to a first surface of the cover member which faces inward and is opposite to a second surface of the cover member that faces outward and comes into contact with the living body, and
   in a state in which the detecting device is not adhered to the cover member, an end portion on an opposite side of the first light-emitting unit from the first light-receiving unit overlaps the first light-blocking filter when viewed from a normal direction of the flexible substrate.

2. The detecting device according to claim 1, further comprising:
   a second light-blocking filter configured to block light traveling toward the first light-receiving unit, wherein
   when viewed from the normal direction of the flexible substrate, in the state in which the detecting device is not adhered to the cover member, an end portion on an opposite side of the first light-receiving unit from the first light-emitting unit overlaps the second light-blocking filter when viewed from the normal direction of the flexible substrate.

3. The detecting device according to claim 1, further comprising:
   a second light-receiving unit, a third light-receiving unit, and a fourth light-receiving unit that are provided at the flexible substrate and configured to receive light, based on the light exiting from the first light-emitting unit, from the living body, wherein
   the second light-receiving unit, the third light-receiving unit, and the fourth light-receiving unit are constituted by a flexible organic photodetector, and
   on a main surface of the flexible substrate,
   the first light-receiving unit and the second light-receiving unit are aligned in a first direction,
   the third light-receiving unit and the fourth light-receiving unit are aligned in a second direction intersecting the first direction, and
   the first light-emitting unit is provided between the first light-receiving unit and the second light-receiving unit, and is provided between the third light-receiving unit and the fourth light-receiving unit.

4. The detecting device according to claim 3, further comprising:
   a second light-emitting unit, a third light-emitting unit, and a fourth light-emitting unit that are provided at the flexible substrate and configured to emit light toward the living body, wherein
   the second light-emitting unit, the third light-emitting unit, and the fourth light-emitting unit are constituted by a flexible organic light-emitting diode, and
   on the main surface of the flexible substrate,
   the first light-emitting unit and the second light-emitting unit are aligned in the first direction, the third light-emitting unit and the fourth light-emitting unit are aligned in the second direction, and the first light-receiving unit is provided between the first light-emitting unit and the second light-emitting unit, and is provided between the third light-emitting unit and the fourth light-emitting unit.

5. The detecting device according to claim 1, wherein the first light-emitting unit and the first light-receiving unit are aligned in a first direction at the flexible substrate, and when being adhered to the living body, the detecting device is deformed into a curved shape bent into an arc in the first direction.

6. The detecting device according to claim 1, wherein the first light-receiving unit surrounds the first light-emitting unit on a main surface of the flexible substrate.

7. A measuring device, comprising:

the detecting device according to claim 1; and an information analysis unit configured to identify biological information from a detection signal indicating a detection result obtained by the detecting device.

* * * * *